United States Patent
Fogh-Hansen

(10) Patent No.: US 9,352,552 B2
(45) Date of Patent: May 31, 2016

(54) SYSTEM AND METHOD FOR REGULATING AND MEASURING FLOW

(71) Applicant: Tresu A/S, Bjert (DK)

(72) Inventor: Christian Fogh-Hansen, Bjert (DK)

(73) Assignee: Tresu A/S, Bjert (DK)

( * ) Notice: Subject to any disclaimer, the term of this patent is extended or adjusted under 35 U.S.C. 154(b) by 0 days.

(21) Appl. No.: 14/397,286

(22) PCT Filed: Mar. 20, 2013

(86) PCT No.: PCT/DK2013/050079
§ 371 (c)(1),
(2) Date: Oct. 27, 2014

(87) PCT Pub. No.: WO2013/159777
PCT Pub. Date: Oct. 31, 2013

(65) Prior Publication Data
US 2015/0114242 A1    Apr. 30, 2015

(30) Foreign Application Priority Data

Apr. 27, 2012    (DK) ................................ 2012 70213

(51) Int. Cl.
| | |
|---|---|
| *B41F 31/08* | (2006.01) |
| *B41F 33/00* | (2006.01) |
| *B41F 31/00* | (2006.01) |
| *F04B 49/06* | (2006.01) |
| *G01F 3/02* | (2006.01) |

(Continued)

(52) U.S. Cl.
CPC .............. *B41F 31/08* (2013.01); *B41F 31/005* (2013.01); *F04B 9/14* (2013.01); *F04B 49/06* (2013.01); *F04B 49/065* (2013.01); *G01F 3/02* (2013.01); *G05D 24/02* (2013.01); *B41P 2233/11* (2013.01); *B41P 2251/10* (2013.01); *B41P 2251/11* (2013.01); *F04B 2205/09* (2013.01); *F04B 2205/14* (2013.01); *G01N 11/02* (2013.01); *G01N 2011/006* (2013.01); *G01N 2011/0046* (2013.01); *G01N 2011/0053* (2013.01)

(58) Field of Classification Search
CPC ...... B41F 31/08; B41F 31/005; B41F 33/025; B41F 33/02; B41P 2233/30; B41P 2251/10
See application file for complete search history.

(56) References Cited

U.S. PATENT DOCUMENTS

| | | |
|---|---|---|
| 2,590,538 A | 3/1952 | Huck |
| 5,027,661 A | 7/1991 | Desaulniers et al. |

(Continued)

FOREIGN PATENT DOCUMENTS

| | | |
|---|---|---|
| CN | 2709163 Y | 7/2005 |
| CN | 201506069 U | 6/2010 |

(Continued)

*Primary Examiner* — Matthew G Marini
*Assistant Examiner* — Leo T Hinze
(74) *Attorney, Agent, or Firm* — Roberts Mlotkowski Safran & Cole, P.C.; David S. Safran

(57) ABSTRACT

A method for regulating the flow of a viscosity-dependent liquid in a graphic process, including a pump (5) configured for pumping a viscosity-dependent liquid (3) from a first container (4) and to a graphic printing machine (1), and wherein the viscosity of the liquid (3) affects operation of the pump (5), a sensor (8) connected with the pump (5) and which is configured to measure at least one of the operational parameters of the pump (5), and a controller (9) connected with the sensor (8) and which is configured to analyze the data from the sensor (8). The controller (9) determines the viscosity of the liquid (3) from the measured operational parameters of the pump (5) and generates a control signal (17) from the measured viscosity, based on which the viscosity of the liquid (3) pumped through the pump (5) can be adjusted.

11 Claims, 2 Drawing Sheets

(51) Int. Cl.
*G05D 24/02* (2006.01)
*F04B 9/14* (2006.01)
*G01N 11/00* (2006.01)
*G01N 11/02* (2006.01)

(56) References Cited

U.S. PATENT DOCUMENTS 5,330,576 A * 7/1994 Clauditz ............ B41F 23/08
118/602

6,546,866 B1 4/2003 Adachi et al.
2009/0288598 A1* 11/2009 Riga, Jr. ............ B05C 1/0813
118/693

FOREIGN PATENT DOCUMENTS

| EP | 1 138 487 A2 | 10/2001 |
| JP | 62-297151 A | 12/1987 |
| WO | 2010/034660 A1 | 4/2010 |
| WO | 2011/018536 A1 | 2/2011 |

* cited by examiner

SYSTEM AND METHOD FOR REGULATING AND MEASURING FLOW

BACKGROUND OF THE INVENTION

1. Field of the Invention

The present invention concerns a system for regulating the flow of an ink in a graphic process, including:
  a reciprocating positive displacement pump, e.g., a piston or membrane pump, connected to a first container via a first liquid conduit and to a printing module in a graphic printing machine via a second liquid conduit, the pump is configured for pumping an ink from the first container and to the graphic printing unit, and wherein the viscosity of the ink affects operation of the pump;
  a sensor connected with the pump and which is configured to measure at least the pump strokes in the pump; and
  a controller connected with the sensor and which is configured to analyse the data from the sensor and determine the number of pump strokes over a predetermined time period.

The present invention also concerns a method for regulating the flow of an ink in a graphic process, including the following steps:
  pumping an ink by means of a reciprocating positive displacement pump, e.g., a piston or membrane pump, from a container and to a printing module (1a) in a graphic printing unit, and wherein the viscosity of the ink affects operation of the pump;
  measuring at least the pump strokes in the pump by means of a sensor; and
  wherein data from the sensor are analyzed and the number of pump strokes over a predetermined period of time are determined in a controller.

2. Description of Related Art

Professional graphic printing machines today need careful control and composition of the various printing inks which are conducted into the printing module in the printing machine in order to attain correct color intensity, brilliance and rubbing resistance on the finished printed matter or article. Therefore, it is necessary to control various properties of each single ink, including viscosity, color composition (mix of ink colors), pigmenting, bonding capability, temperature, flow, etc. during the printing process.

Various systems and methods for measuring and controlling the flow of printing inks are described in the literature. Similarly, various systems and methods for regulating the properties of the inks are described in the literature.

European Patent Application EP 1 138 487 A2 and corresponding U.S. Pat. No. 6,546,681 disclose a system and a method for measuring and regulating the viscosity of ink in a printing machine where the measuring apparatus for measuring the viscosity includes two rotating parts which are magnetically interconnected by means of magnets provided in both parts, of which one part is disposed in the liquid flow after the pump, and the other part is disposed outside the liquid flow. An electric motor rotates the part disposed outside the liquid flow which in turn rotates the other part by means of the magnetic field generated by the magnets. The electric motor is connected with a control unit regulating the speed of the motor so that the parts are rotated at constant speed. The control unit detects the power consumption used for rotating the parts at the constant speed, and then calculates the viscosity of the ink. At least one flowmeter is disposed either before or after the apparatus in order to ensure constant flow through the measuring apparatus. The viscosity is automatically regulated by means of a dosing apparatus which adds a diluent to the ink determined by the measured viscosity.

This system uses up to several measuring units disposed between the pump and the printing unit provided in the printing machine for measuring the flow and viscosity of the ink and a relatively complex regulating system for controlling the viscosity of the ink. These units increase the complexity of the entire plant, raising the cost of the entire plant considerably. Moreover, the various measuring units in the liquid flow require regular maintenance in order to avoid erratic measurements and clogging that may cause the plant to be shut down which in turn raises the total production costs and costs of maintenance.

U.S. Pat. No. 5,027,661 A1 describes a system and a method for measuring the volume of ink in a printing machine wherein the system includes a microphone or a pressure sensor for measuring the outgoing air pressure or pressure variations in the flow to the pump. The microphone/sensor is used for detecting the pump strokes of the pump and is connected to a microprocessor which calculates the number of pump strokes, the speed of the pump and the volume of each pump stroke for the pump in question. The pump strokes are used to determine if the container from which the pump is pumping is about to run dry. The microprocessor can control several pumps individually in order to achieve correct color composition.

This system has the advantage that it does not require one or more external flowmeters disposed in the liquid flow in order to determine the volume of the ink, a fact which contributes to minimise the total costs of the plant.

However, this system has the drawback that it is only possible to determine the volume of the ink from the pump strokes. Since the viscosity influences how much ink is pumped out for each pump stroke, it is necessary manually to determine the viscosity by means of known measuring techniques and to dilute the ink manually. If the viscosity changes, it is necessary to regulate the speed of the pump (number of pump strokes) in order to maintain a constant flow of ink to the printing machine.

U.S. Pat. No. 2,590,538 discloses a rotogravure printing system having a pump configured to pump the ink from a first reservoir to a second reservoir in the printing device. The pump is arranged between a mixing chamber and a manual adjustable valve. The mixing chamber has two inlets connected to the first reservoir and a third reservoir holding a diluent respectively. A pressure sensor connected to a T-junction is arranged between the pump and the adjustable valve. An electrically controlled valve is activated when the pressure in the ink conduit reaches a threshold value, whereby diluent is led into the mixing chamber. As the pressure in the ink conduit drops below the threshold value, the valve is deactivated and the supply of diluent is stopped.

SUMMARY OF THE INVENTION

The object of the present invention is to provide a system and a method that will solve the problems of the prior art in an alternative way.

Another object of the present invention is to provide a system and a method which enable controlling the volume and the viscosity in a more simple way.

A further object of the present invention is to provide a system and a method that minimize the time in which the plant is shut down for maintenance and repair.

Yet another object of the present invention is to provide a system and a method that reduce the costs of installing the plant and for maintaining the plant.

The present invention provides for solving the problems of the prior art by providing a system for regulating the flow of an ink in a graphic process, characterized in that the controller is configured to determine the viscosity of the ink based on the measured number of pump strokes in the pump; and that the controller is configured to generate a control signal from the measured/determined viscosity; and the system includes a dosing unit configured to receive the control signal from the controller and to add a predetermined amount of a diluent from a second container into the first container holding the ink for regulating the viscosity of the ink.

Hereby is provided a system which in a simple and efficient way determines an expression for viscosity and thereby the flow of ink based on how efficient the pump is to pump the ink further on in the system. Hereby the need for manual control of the viscosity is eliminated by means of a viscometer or by using an automatic viscometer disposed in the flow of ink, a fact with much influence on the price of a plant. Also, the need for flowmeters disposed in the ink flow is eliminated as the flow can be determined from the efficiency of the pump (also called useful effect), constituting an appreciable cost saving as well.

It is possible to detect variations in the viscosity by monitoring one or more of the operational parameters of the pump such as the resistance (also called system resistance) exerted on the pump by the liquid is dependent on the viscosity of the liquid. The higher viscosity of the liquid, the more resistance is exerted by the liquid on the pump, and the more energy is to be supplied to the pump in order to perform a complete pump stroke. Since the power supply is kept constant, this will reduce the number of pump strokes over a predetermined period of time.

The viscosity of the liquid may alternatively be determined from the power supply needed for maintaining an approximately constant flow through the pump, whereby the pressure in the liquid conduit can be kept approximately constant. In this embodiment, the sensor will be configured to measure the energy consumption in the pump, e.g., the electric power consumption or the pressure/flow in the compressed air supplied to the pump.

The pump is designed as a piston pump or a membrane pump which is typically driven by compressed air, but can also be driven in other ways, or be an electrically driven pump of suitable type.

These types of pumps may advantageously be used in a graphic printing process as these pumps are suited for small volume flows and where the viscosity of the liquid pumped through the pump affects the output of these pumps.

The dosing unit can automatically regulate the viscosity of the ink by adding a diluent in the form of alcohol, water or similar, either directly in the container in which the ink is stored, or in the ink flow before or after the pump. The need of manually adding diluent when the viscosity becomes too high is hereby eliminated. Moreover, it is possible to avoid the inaccuracies that may occur in connection with measuring/weighing the diluent.

According to an embodiment of the invention, the pump is connected to a control unit which is configured to drive the pump with constant power supply.

By determining the viscosity and thereby the flow of ink from the efficiency of the pump, it is possible to operate the pump with approximately constant power supply; hereby, the need of regulating the pump speed in order to compensate for variations in the viscosity is eliminated. The service life of the pump may hereby be extended and the energy consumption in the pump can be reduced as no regulation of the speed and thus the energy consumption in the pump is performed in order to maintain a constant flow through the pump. The pump can be powered by a constant supply voltage, a constant supply current or by means of compressed air at a constant pressure, where the term constant is to be regarded as approximately constant as the actual parameter is attempted kept constant by control measures.

In an embodiment of the invention, the system includes a user interface configured to show the value of the measured/determined viscosity and the measured flow, and where an operator can adjust at least one of the operational parameters of the pump.

The operator may hereby visually read an expression for the flow and for the viscosity of the ink, and regulate the flow or one of the other operational parameters of the pump. The need of the operator manually measuring the viscosity is hereby eliminated as the value can be read on the meter or on the display. The reading of the viscosity may advantageously be provided with different colors, including green, yellow and red, which show whether the viscosity is within the wanted tolerances. The visual values, e.g., viscosity, may advantageously be only with relative values and deviations relative to a relative set point.

According to an embodiment of the invention, the system includes an alarm unit configured to receive the control signal from the controller and to generate a visual or acoustic alarm based on the control signal.

Hereby it is possible to inform an operator of the plant that the viscosity is too high and that a diluent has to be added. The operator will then be able to activate the dosing unit or add the diluent manually. The need for regular control of the viscosity by the operator so as to ensure that the ink has the wanted viscosity is hereby eliminated.

The present invention provides for solving the problems of the prior art by providing a method for regulating the flow of an ink in a graphic process, characterized in that the controller determines the viscosity of the ink based on the measured number of pump strokes in the pump; and the viscosity of the ink pumped through the pump is changed by adding a predetermined amount of a diluent to the ink in the first container by means of a dosing unit controlled by the controller.

Hereby it is possible to determine the viscosity or an expression of the viscosity in the form of a value and thereby the flow of ink, based on how efficient the pump is to pump the ink further on in the system, in a simple way. Also, the need for manual control of the viscosity is eliminated by means of a viscometer or by using an automatic viscometer disposed in the flow of ink. Furthermore, the need for flowmeters disposed in the ink flow can be reduced or entirely eliminated as the flow can be determined from the efficiency of the pump (also called useful effect).

The sensor measures the number of pump strokes in the pump over a predetermined period of time.

Hereby it is possible to detect variations in the viscosity as the resistance (also called system resistance) exerted on the pump by the liquid is dependent on the viscosity of the liquid. The higher viscosity of the liquid, the more resistance is exerted by the liquid on the pump, and the more energy is used by the pump in order to perform a complete pump stroke. Since the power supply is kept constant, this will reduce the number of pump strokes over a predetermined period of time. Variations in the viscosity may also be detected by measuring other operational parameters, such as the pressure in the pump.

The viscosity of the liquid is changed by adding a predetermined amount of a diluent to the viscosity-dependent liquid in the first container by means of a dosing unit controlled by the controller.

Hereby, the viscosity of the ink can be adjusted automatically by adding a diluent in the form of alcohol, water or similar, either directly in the container in which the ink is stored, or in the ink flow before or after the pump. Also, the need of manually adding diluent when the viscosity becomes too high is hereby eliminated. Moreover, it is possible to avoid the inaccuracies that may occur in connection with measuring/weighing the diluent.

According to an embodiment of the invention, the pump is driven with a constant or approximately constant power supply from a control unit, which e.g., can be compressed air with constant pressure or a constant current or supply voltage for an electric motor.

By determining the flow, and in particular, an expression of the viscosity of the ink from the efficiency of the pump, it is possible to operate the pump with approximately constant power supply; hereby, the need for regulating the pump speed in order to compensate for variations in the viscosity is eliminated. The service life of the pump can hereby be extended and the energy consumption in the pump can be reduced as no regulation of the pump speed is performed in order to maintain a constant flow through the pump.

According to an embodiment of the invention, the controller activates the dosing unit when the number of pump strokes is less than or equal to a first threshold value. According to a particular embodiment of the invention, the controller deactivates the dosing unit when the number of pump strokes is greater than or equal to a second threshold value.

According to a particular embodiment of the invention, the measured/determined viscosity and the measured/determined flow are displayed on a user interface at which an operator can regulate at least one of the operational parameters of the pump.

For an operator, it is hereby possible to see the values of the various operational parameters measured during the printing process, and based on these perform a regulation of one or more operational parameters. This is particularly advantageous in connection with commencing new printing tasks using different inks, or when needing some other properties of the inks in order to achieve the desired effect. Moreover, it is very advantageous during continuous operation to be able to maintain the same viscosity in the ink.

According to an embodiment of the invention, the controller activates an alarm unit which generates a visual or acoustic alarm if the viscosity is greater than or equal to a first threshold value.

Hereby it is possible to inform an operator of the plant that the viscosity is too high and that a diluent has to be added. The operator will then be able to activate the dosing unit or add the diluent manually. The need for regular control of the viscosity by the operator so as to ensure that the ink has the wanted viscosity is hereby eliminated.

The invention is described in the following with reference to the drawings

DETAILED DESCRIPTION OF THE INVENTION

In the explanation of the figures, identical or corresponding elements will be provided with the same designations in different figures. Therefore, no explanation of all details will be given in connection with each single figure/embodiment.

By the term "ink" is meant any viscosity-dependent liquid used in a graphic printing process for producing a printed matter with the desired properties, including colors/inks with any kind of pigmenting, UV-colors and lacquers, water-/alcohol-/oil-based inks and lacquers, any type of ink/lacquer and similar liquids.

Figure 1:
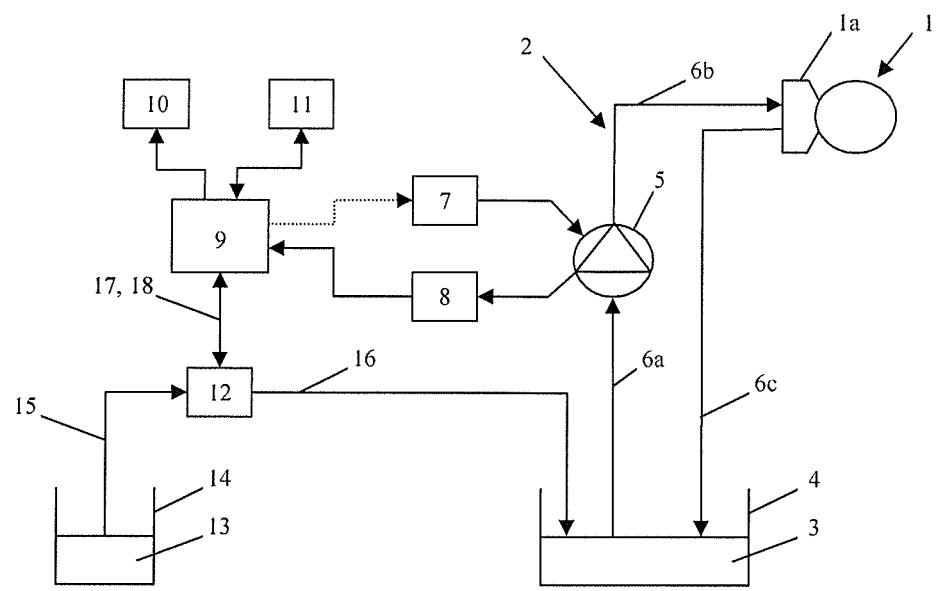
FIG. 1 shows a simplified schematic of the system according to an embodiment of the invention.

FIG. 1 shows a simple layout of the system according to the invention, including a graphic printing machine 1 connected to a number of circulatory circuits 2 that are configured to supply one or more inks to a printing module 1a inside the printing machine 1. The printing machine 1 is of known construction, and thus, need not be described in detail.

The circulatory circuit 2 includes a reservoir 4 in the form of a container in which the ink 3 is stored, and a pump 5 configured to pump the ink 3 further on into the printing machine 1. The reservoir 4 is connected to the pump 5 via liquid conduit 6a which in turn is connected to the printing module 1a via a second liquid conduit 6b. The printing module 1a in the printing machine 1 is connected to the reservoir 4 via a return liquid conduit 6c so that excess ink 3 can be returned to the reservoir 4. The return liquid conduit 6c may include a return pump (not shown) configured to pump the excessive ink 3 back to the reservoir. The return pump may have the same configuration as the pump 5 or a different configuration, and can be controlled dependent on or independent of the pump 5. The liquid conduits 6 may be an arrangement of pipes or hoses.

The pump 5 is configured as a piston pump, a membrane pump or an electrically powered pump connected to a control unit 7 that may be connected to a controller 9. The control unit 7 is configured to drive one or more movable parts in the pump 5 by means of any electric, electromagnetic, mechanical, compressed air or liquid connection. The movable parts are designed such that when the parts move back and forth, the ink 3 is conducted through the pump 5. The pump 5 can be configured as any other type of pump where one or more operational parameters (pressure, flow, power/energy consumption, supply voltage, pump strokes and similar) and thereby the efficiency (also called useful effect) of the pump 5 are influenced by the viscosity of the ink 3.

One or more sensors 8 are connected to the pump 5 such that they detect the resistance (system resistance) exerted by the ink 3 on the pump 5 by measuring one or more operational parameters in the pump 5. The sensor 8 is connected to a controller 9 which, based on the measured operational parameters and thereby the resistance, determines the viscosity or an expression thereof, and thereby also the flow of the ink 3.

In a particular embodiment, the sensors 8 are configured so that they measure the pump strokes in the pump and generate an electric signal for each pump stroke. A pump stroke is defined as being a complete pump stroke, i.e., from the piston/membrane leaves its initial position until it returns to its initial position. In a second embodiment, the sensors 8 are configured such that they measure the length of the movement which the piston/membrane performs at each pump stroke. Alternatively, more than one type of sensor 8 can be connected to the pump 5 such that the sensors 8 detect more than one of the operational parameters of the pump 5.

In a particular embodiment, the number of pump strokes is accumulated over one or more predetermined periods of time $T_1$ in the controller 9, after which the controller 9 determines the viscosity of the ink 3. The number of pump strokes may alternatively be accumulated in the sensor 8 and then be transmitted to the controller 9. The period of time $T_1$ can be determined as one minute; however, depending on the inertia (sluggishness) in the system and the desired measuring accuracy the period of time $T_1$ can be shorter or longer than one minute.

An alarm unit 10 in the form of an acoustic, a visual or a vibrating alarm can be connected to the controller 9 and be configured to generate an acoustic, a visual or a vibrating alarm based on a control signal 17 from the controller 9.

A user interface 11 in the form of a touch-sensitive display or an operating panel including a number of meters and buttons/switches can be connected with the controller 9. The user interface 11 is configured so that an operator may visually read various measured parameters in the plant and perform adjustments of one or more of these parameters, e.g., adjusting the viscosity and the flow.

In a particular embodiment, the controller 9 is configured such that the controller 9 determines the flow, e.g., the volume flow, and the viscosity of the ink 3. The user interface 11 is designed as a graphic user interface wherein the measured/determined values of flow and viscosity are graphically depicted. Via the user interface 11, the operator can set/enter the desired parameters, e.g., the wanted flow, and thereby control the individual units connected to the controller 9, e.g., the pump 5, via the control unit 7.

In another particular embodiment, the controller 9 is connected to one or more dosing units 12 which are configured to feed a predetermined amount (volume) of a diluents 13 to the reservoir 4 in which the ink 3 is stored, so as to dilute the ink 3 in order to reduce the viscosity. The dosing unit 12 is connected by a liquid conduit to a reservoir 14 in the form of a container or external unit in which the diluent 13 is stored. The dosing unit 12 is in turn connected to the reservoir 4 via a second liquid conduit 16. The liquid conduits 15, 16 can be an arrangement of pipes or hoses. The dosing unit 12 can be designed as a pump or valve (not shown) configured to pump or conduct the diluent from the reservoir 14 into the reservoir 4.

A stirrer (not shown) configured to stir the ink 3 can be disposed in the reservoir 4 so that the diluent 13 is mixed with the ink 3. The stirrer can be controlled by the controller 9.

The controller 9 can be connected to a number of circulatory circuits 2 which include each their reservoir 4 with each their ink 3. The controller 9 can determine the viscosity of each of the inks 3 and perform an individual or group-wise regulation of the viscosity of each of the inks 3. One or more circulatory circuits 2 can be connected to the same dosing unit 12.

Figure 2:
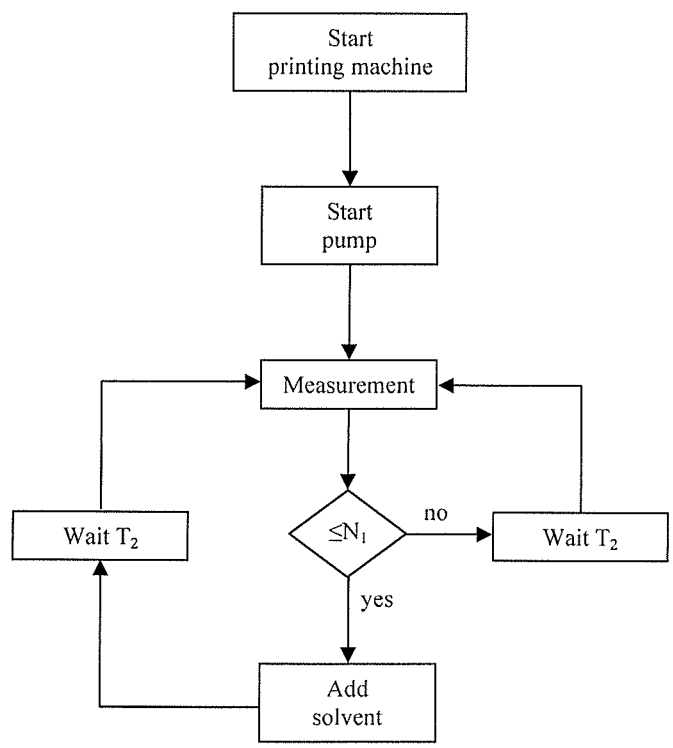
FIG. 2 is a flow chart of a method for regulating the viscosity according to a first embodiment of the invention.

The function of the system will be described in further detail in connection with FIGS. 2 & 3. FIG. 2 shows a method for regulating the viscosity according to a first embodiment of the invention.

In connection with starting of the plant, the printing machine 1 and the pump 5 are activated, after which the pump 5 commences pumping the ink 3 to the printing module in the printing machine 1. After starting the pump 5, the controller 9 determines the viscosity of the ink 3 based on the measured operational parameters of the pump after which the viscosity is compared with the first threshold value $N_1$.

If the measured viscosity is equal to or greater than the first threshold value $N_1$, the controller 9 generates a control signal 17 which is transmitted to the alarm unit 10 and/or the dosing unit 12. If the control signal 17 is transmitted to the alarm unit 10, it will then generate an alarm calling the attention of the operator of the plant to the fact that the viscosity of the ink 3 is too high. If the control signal 17 is transmitted to the dosing unit 12, the dosing unit 12 is activated after which a fixed, predetermined amount of the diluent 13 is added to the ink 3. When this process is finished, the dosing unit 12 returns a response signal 18 to the controller 9.

Alternatively, the controller 9 can adjust the amount of diluent 13 in relation to the amount of ink 3 in the reservoir 4 and to some extent the amount of ink 3 circulating in the circuit 2 as well. A better regulation of the viscosity of the ink 3 may thereby be achieved as it is possible to allow for the inertia (sluggishness) in the circuit 2.

After diluting the ink 3, a new measurement of the viscosity is performed after a predetermined period of time $T_2$ which may be equal to or greater than the period of time $T_1$.

If the measured viscosity falls below the first threshold value $N_1$, a new measurement is performed after a new period of time $T_2$. If not, the dosing unit 12 is activated again and/or the alarm unit 10 remains activated.

In a particular embodiment, the number of pump strokes is compared with the threshold value $N_1$ instead of the measured viscosity. In this embodiment, the dosing unit 12 and/or the alarm unit 10 are/is activated if the number of pump strokes is equal to or less than the first threshold value $N_1$.

Figure 3:
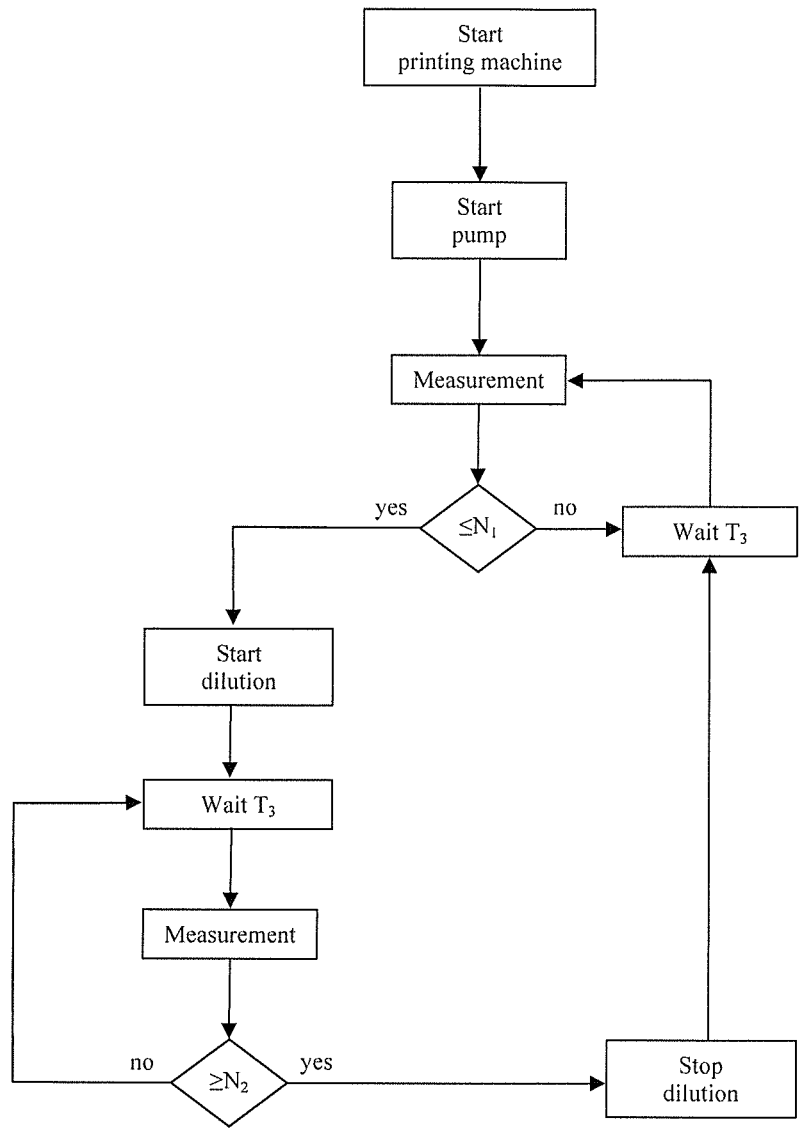
FIG. 3 is a flow chart of a method for regulating the viscosity according to a second embodiment of the invention.

FIG. 3 shows a method for regulating the viscosity according to a second embodiment of the invention. This embodiment differs from the one in FIG. 2 in that the dosing unit 12 is only deactivated when the viscosity or the number of pump strokes reach a second threshold value $N_2$.

Starting of the plant and the pump 5 occurs in the same way as described in connection with FIG. 2.

If the measured viscosity is equal to or greater than the first threshold value $N_1$, or alternatively if the number of pump strokes is equal to or less than the first threshold value $N_1$, the controller 9 generates a control signal 17 which is transmitted to the alarm unit 10 and/or the dosing unit 12. In the control signal 17 is transmitted to the alarm unit 10, the latter will then generate an alarm calling the attention of the operator of the plant to the fact that the viscosity of the ink 3 is too high. If the control signal 17 is transmitted to the dosing unit 12, the dosing unit 12 is activated after which a predetermined amount of the diluent 13 is continuously added to the ink 3.

After a predetermined period of time $T_3$, which can be equal to or less than the period of time $T_2$, a new measurement is performed.

If the measured viscosity is above the second threshold value $N_2$, or alternatively if the number of pump strokes is below the second threshold value $N_2$, the dosing unit 12 remains activated. If the measured viscosity is below the second threshold value $N_2$, or alternatively if the number of pump strokes is above the second threshold value $N_2$, the dosing unit 12 is deactivated. A new measurement is performed after a new period of time $T_3$.

Hereby, the amount of diluent 13 can be adjusted in relation to the amount of ink 3 in the reservoir 4 and to some extent the amount of ink 3 circulating in the circuit 2 as well. A better regulation of the viscosity of the ink 3 may thereby be achieved as it is possible to allow for the inertia (sluggishness) in the circuit 2. Moreover, it is possible to perform continuous dilution of the ink 3 within a certain range of pump strokes.

What is claimed is:

1. A system for regulating the flow of an ink in a graphic process, including:

a reciprocating positive displacement pump connected to a first container via a first liquid conduit and to a printing module in a graphic printing machine via a second liquid conduit, the pump is configured for pumping an ink from the first container and to the graphic printing machine, and wherein the viscosity of the ink affects operation of the pump;

a sensor connected with the pump and configured to measure at least the pump strokes in the pump; and a controller connected with the sensor and configured to analyse the data from the sensor and determine the number of the pump strokes over a predetermined period of time ($T_1$); wherein the controller is configured to determine the viscosity of the ink based on the measured number of pump strokes in the pump;

the controller is configured to generate a control signal from the measured/determined viscosity; and the system includes a dosing unit configured to receive the control signal from the controller and to add a predetermined amount of a diluent from a second container into the first container holding the ink for regulating the viscosity of the ink.

2. System according to claim 1, wherein the pump is connected to a control unit which is configured to drive the pump (5) with an approximately constant power supply.

3. System according to claim 1, wherein the pump is a pump driven by compressed air or an electrically powered pump.

4. System according to claim 1, wherein the system includes a user interface configured to show the value of the measured/determined viscosity and where at least one of the operational parameters of the pump is operator adjustable.

5. System according to claim 1, wherein the system includes an alarm unit configured to receive the control signal from the controller and to generate a visual or acoustic alarm based on the control signal.

6. System according to claim 1, wherein the controller is also configured to regulate the flow of the ink based on the measured number of pump strokes in the pump and wherein the system includes a user interface configured to show a value of the flow and to enable at least one of the operational parameters of the pump to be operator adjustable.

7. A method for regulating the flow of an ink in a graphic process, including the following steps:

pumping an ink by means of a reciprocating positive displacement pump, from a container to a printing module in a graphic printing machine, and wherein the viscosity of the ink affects operation of the pump ;

measuring at least the pump strokes in the pump by means of a sensor; and wherein the data from the sensor are analysed and the number of pump strokes over a predetermined period of time ($T_1$) are determined in a controller; wherein:

the controller determines the viscosity of the ink based on the measured number of pump strokes in the pump; and the viscosity of the ink pumped through the pump is changed by adding a predetermined amount of a diluent to the ink in the first container by means of a dosing unit controlled by the controller.

8. Method according to claim 7, wherein the pump is driven with approximately constant power supply from a control unit.

9. Method according to claim 7, wherein the measured/determined viscosity is displayed on a user interface at which an operator can regulate at least one of the operational parameters of the pump.

10. Method according to claim 7, wherein the controller activates an alarm unit which generates a visual or acoustic alarm if the number of pump strokes are less than or equal to a first threshold value.

11. Method according to claim 7, wherein the controller also regulates the flow of the ink based on the measured number of pump strokes in the pump and wherein the flow is displayed on a user interface at which an operator can regulate at least one of the operational parameters of the pump.

* * * * *